United States Patent
Carlsson (10) Patent No.: US 12,303,357 B2
(45) Date of Patent: *May 20, 2025

(54) FIBER MATERIALS WITH IMPROVED PROPERTIES FOR USE IN WOUND TREATMENT

(71) Applicant: MÖLNLYCKE HEALTH CARE AB, Gothenburg (SE)

(72) Inventor: Erik Carlsson, Särö (SE)

(73) Assignee: Mölnlycke Health Care AB, Mölndal (SE)

( * ) Notice: Subject to any disclaimer, the term of this patent is extended or adjusted under 35 U.S.C. 154(b) by 0 days.

This patent is subject to a terminal disclaimer.

(21) Appl. No.: 18/646,974

(22) Filed: Apr. 26, 2024

(65) Prior Publication Data

US 2024/0293262 A1    Sep. 5, 2024

Related U.S. Application Data

(63) Continuation of application No. 18/146,501, filed on Dec. 27, 2022, now Pat. No. 11,998,425, which is a
(Continued)

(30) Foreign Application Priority Data

Jan. 25, 2017    (EP) .................... 17153138

(51) Int. Cl.
*A61F 13/0206*    (2024.01)
*A61F 13/0203*    (2024.01)
(Continued)

(52) U.S. Cl.
CPC ...... *A61F 13/0209* (2013.01); *A61F 13/0213* (2013.01); *A61L 15/24* (2013.01);
(Continued)

(58) Field of Classification Search
CPC .... A61F 2013/5078; A61F 2013/53007; A61F 2013/0819; A61F 2013/530569; A61F 2013/530583; A61F 2013/530613
See application file for complete search history.

(56) References Cited

U.S. PATENT DOCUMENTS

| | | |
|---|---|---|
| 2,273,636 A | 2/1942 | Gellendien et al. |
| 4,035,217 A | 7/1977 | Kennette et al. |
| (Continued) | | |

FOREIGN PATENT DOCUMENTS

| | | | |
|---|---|---|---|
| CA | 3121872 C | * 9/2023 | ............ A01N 59/16 |
| CN | 1310634 A | 8/2001 | |
| (Continued) | | | |

OTHER PUBLICATIONS

International Search Report and Written Opinion were mailed on Mar. 8, 2018 by the International Searching Authority for International Application No. PCT/EP2018/051064, filed on Jan. 17, 2018 and published as WO 2018/137979 on Aug. 2, 2018(Applicant-Molnlycke Health Care AB) (10 Pages).
(Continued)

*Primary Examiner* — Kim M Lewis
(74) *Attorney, Agent, or Firm* — Ballard Spahr LLP (57) ABSTRACT

Described is a fiber material comprising a substrate of non-ionic, non-woven fibers, and at least one additional component, which is an agent that comprises at least one group capable of forming a hydrogen bond, wherein a combination of the substrate and the agent causes the fiber material to have an increased wet tensile strength of at least 5%, as measured in accordance with EN 29073-3:1992, as compared to an otherwise identical fiber material without the agent. The fiber material can be of use in various fields, in
(Continued)

particular household products, hygiene products, and the like. These fiber materials are of particular use in wound treatment.

18 Claims, 2 Drawing Sheets

Related U.S. Application Data continuation of application No. 16/480,049, filed as application No. PCT/EP2018/051064 on Jan. 17, 2018, now Pat. No. 11,559,440.

(51) Int. Cl.
*A61L 15/24* (2006.01)
*A61L 15/26* (2006.01)
*A61L 15/28* (2006.01)
*A61L 15/46* (2006.01)
*A61L 15/60* (2006.01)
*D04H 1/4258* (2012.01)
*D04H 1/4309* (2012.01)

(52) U.S. Cl.
CPC ............... *A61L 15/26* (2013.01); *A61L 15/28* (2013.01); *A61L 15/46* (2013.01); *A61L 15/60* (2013.01); *D04H 1/4258* (2013.01); *D04H 1/4309* (2013.01); *A61L 2300/404* (2013.01)

(56) References Cited

U.S. PATENT DOCUMENTS

| | | | |
|---|---|---|---|
| 5,538,783 A | 7/1996 | Hansen et al. | |
| 5,547,745 A | 8/1996 | Hansen et al. | |
| 5,607,759 A | 3/1997 | Hansen et al. | |
| 5,840,787 A | 11/1998 | West et al. | |
| 6,783,852 B2 | 3/2004 | Inada et al. | |
| 11,559,440 B2 * | 1/2023 | Carlsson | A61F 13/0213 |
| 11,998,425 B2 * | 6/2024 | Carlsson | A61L 15/46 |
| 2004/0058605 A1 | 3/2004 | Hansen | |
| 2009/0169606 A1 | 7/2009 | Andersen et al. | |
| 2013/0274415 A1 | 10/2013 | Schmitz et al. | |
| 2013/0323195 A1 | 12/2013 | Schmitz et al. | |
| 2017/0002511 A1 | 1/2017 | Duncker-Rakow et al. | |

FOREIGN PATENT DOCUMENTS

| | | |
|---|---|---|
| CN | 1495297 A | 5/2004 |
| CN | 102844009 A | 12/2012 |
| CN | 103374766 A | 10/2013 |
| JP | H08500270 A | 1/1996 |
| JP | 2004143653 | 5/2004 |
| JP | 2009518319 | 5/2009 |
| WO | WO 2013/041620 | 3/2013 |
| WO | WO2018/137979 | 8/2018 |

OTHER PUBLICATIONS

Elangannan Arunan, et al., IUPAC Definition for "Hydrogen Bond" in Pure Appl. Chem., vol. 83, No. 8, pp. 1637-1641, 2011.

* cited by examiner

PVA  Schematic depiction  Glycerol hydrogen
      of hydrogen bond link  bond link Schematic depiction of polymers
linked by hydrogen bonding

FIBER MATERIALS WITH IMPROVED PROPERTIES FOR USE IN WOUND TREATMENT

CROSS-REFERENCE TO RELATED APPLICATIONS

This application is continuation of U.S. application Ser. No. 18/146,501, filed on Dec. 27, 2022, which is a continuation of U.S. application Ser. No. 16/480,049, filed on Jul. 23, 2019, issued as U.S. Pat. No. 11,559,440 on Jan. 24, 2023, which is a U.S. National Phase Application of International Application No. PCT/EP2018/051064, filed Jan. 17, 2018, which claims priority to European Application No. 17153138.7, filed Jan. 25, 2017, each of which are hereby incorporated by reference in their entirety.

FIELD OF THE INVENTION

The present invention relates to fiber materials with improved properties, in particular improved mechanical properties. These improvements, among others, are achieved by providing a substrate of non-woven fibers, preferably a web of non-woven fibers, together with an agent having at least one, preferably at least two groups capable of forming a hydrogen bond. The resulting fiber materials have, among others, improved tensile strength, in particular wet tensile strength, vis-à-vis fiber materials not treated with such an agent.

While the fiber materials according to the present invention may be of use in various fields, in particular as carrier materials, household products, hygiene products and the like, these fiber materials are of particular use in wound treatment.

The present invention also relates to a method for producing these materials.

BACKGROUND OF THE INVENTION

Fiber materials, in particular fiber materials that are capable to absorb and retain a liquid (fluid), are useful in a variety of applications, including as carrier substrates, household products, hygiene products and in wound treatment. The area of wound treatment poses particular challenges to fiber materials, since not only is adequate fluid management required, but also integrity of the overall product containing the fiber, in particular during application, use and removal. The fiber material, just as the overall wound care product, must also be sterile, safe to use in contact with bodily fluids and, ideally, comfortable to wear for the patient.

US 2013/0323195 discloses high performance fiber materials, as well as an associated method of production. The document further discloses the use of such fibers or fibrous structures as carrier materials, hygiene products, cosmetic products and bandages or wound dressings, containing such fibers or fibrous structures.

An alternative approach to obtain a wound care product, which is not based on modifying the properties of a fiber material, is realized in Geliperm (Geistlich Pharma AG), which is a hydrogel sheet that consists of two different interlaced polymers, i.e. an agar gel and a polyacrylamide. The hydrated sheet form contains about 96% water, 1% agar, and 3% polyacrylamide, whereas the dry sheet form differs from the hydrated form that 35% glycerol are added so that the sheet can rapidly absorb water (see: "*Surgical Dessings and Wound Management*", by Stephan Thomas, Medetec, 2010).

In order to improve or modify properties of fiber materials used in these applications, various approaches have been pursued in the art to physically and/or chemically treat/modify a given fiber material. According to the art, these modifications primarily focus on improving the handling properties of the fiber material.

For example, U.S. Pat. No. 2,273,636 discloses regenerated cellulose products, obtained from aqueous cellulose solutions, which are treated with glycerol derivatives for the purpose of impregnating or softening. In particular, solutions 1.5% glycerol-monomethylether and 1.5% triacetine are described for the purpose of softening of regenerated cellulose products, resulting in soft and elastic cellulose-foils having reduced hygroscopic behavior.

In wound care, fiber materials that are capable of absorbing and retaining fluids are generally preferred over other conceivable substrate materials, already for reasons of improved wound exudate management. Fiber materials that are capable to form gels when coming in contact with a fluid, i.e. can take up fluid, are particularly preferred.

However, wetness and/or swelling (gelling) of the fiber material, and hence the wound care product associated therewith, may lead to problems regarding the stability/integrity of the wound care product, in particular the fiber material component thereof. For example, the overall wound care product may disassociate, either between layers/films and/or within a layer/film. Therefore, fiber materials, in particular gel forming fiber materials should ideally maintain their integrity during use, including during dressing changes, in order to avoid disintegration, decrease in performance and/or the potential that residuals of the dressing remain in the wound.

SUMMARY OF THE INVENTION

In view of the above-mentioned and other drawbacks or unfulfilled needs of the prior art, one object of the present invention is to provide a fiber material having improved stability/integrity, in particular in moist or under wet conditions.

The general concept underlying the present invention is based on the realization that the integrity/stability of a fiber material, in particular the wet tensile strength of a fiber material as described in more detail below, can be improved when said fiber material is brought into contact with an agent that comprises at least one group capable of forming a hydrogen bond, preferably at least two groups capable of forming a hydrogen bond, resulting in a fiber material that is advantageously modified.

According to a first aspect of the invention, these and other objects are achieved by a fiber material comprising:
 a substrate of non-ionic, non-woven fibers, preferably a web of non-ionic, non-woven fibers,
 at least one additional component, which is an agent that comprises at least one group capable of forming a hydrogen bond, preferably at least two groups capable of forming a hydrogen bond.

Preferably, the fiber material is capable of absorbing and retaining a fluid.

In accordance with the present invention, and in particular in the claims, the terms "comprising" and "comprise(s)" do not exclude other elements or steps. Use of the indefinite article "a" or "an" does not exclude a plurality of elements or steps. In particular, more than one (non-ionic or otherwise) type of fiber may be present in the fiber material, as well as more than one agent capable of forming a hydrogen bond may be present in the materials of the present invention. Other suitable materials that are neither fiber materials nor agents capable of forming a hydrogen bond may be present in the fiber materials according to the present invention.

The mere fact that certain measures are recited in mutually different dependent embodiment or claims does not indicate that a combination of these measures cannot be used to advantage.

In accordance with the present invention, a substrate of fibers is any arrangement of fibers that has a larger extension in a (x-y) plane than in the direction perpendicular thereto (z-direction). The substrate is capable to be brought into contact with the at least one agent that comprises at least one group capable of forming a hydrogen bond, preferably at least two groups capable of forming a hydrogen bond. Preferably the fiber substrate has an area weight ("grammage") of 20-500 g/m$^2$, preferably 50-350 g/m$^2$.

In accordance with the present invention, and also in accordance with the universally accepted understanding of the skilled person, a "non-woven" is defined as sheet or web structures bonded together by entangling fiber or filaments mechanically, thermally, or chemically, but not (as is conventionally done for fabrics) by weaving or knitting. Non-wovens are defined by ISO standard 9092 and CEN EN 29092. Non-woven substrates or webs are typically flat, porous sheets that are made directly from separate fibers or from molten plastic or plastic films.

In accordance with the present invention, and also in accordance with the universally accepted definition of the term, a "hydrogen bond" in the feature "at least one group capable of forming a hydrogen bond" is to be understood as relating to an attractive interaction between a hydrogen atom from a molecule or a molecular fragment X-H in which X is more electronegative than H, and an atom or a group of atoms in the same or a different molecule, in which there is evidence of bond formation (see IUPAC Definition for "hydrogen bond" in Pure Appl. Chem., Vol. 83, No. 8, pages 1637-1641, 2011).

As known to the skilled person, and as summarized in the above-mentioned IUPAC reference, a group capable of forming a hydrogen bond can be readily identified using one or any set of the following officially recognized experimental criteria (E1)-(E6):

(E1) The forces involved in the formation of a hydrogen bond X-H•••Y-Z include those of an electrostatic origin, those arising from charge transfer between the donor and acceptor leading to partial covalent bond formation between H and Y, and those originating from dispersion.

(E2) The atoms X and H are covalently bonded to one another and the X-H bond is polarized, the H•••Y bond strength increasing with the increase in electronegativity of X.

(E3) The X-H•••Y angle is usually linear (180°) and the closer the angle is to 180°, the stronger is the hydrogen bond and the shorter is the H•••Y distance.

(E4) The length of the X-H bond usually increases on hydrogen bond formation leading to a red shift in the infrared X-H stretching frequency and an increase in the infrared absorption cross-section for the X-H stretching vibration. The greater the lengthening of the X-H bond in X-H•••Y, the stronger is the H•••Y bond. Simultaneously, new vibrational modes associated with the formation of the H•••Y bond are generated.

(E5) The X-H•••Y-Z hydrogen bond leads to characteristic NMR signatures that typically include pronounced proton deshielding for H in X-H, through hydrogen bond spin-spin couplings between X and Y, and nuclear Overhauser enhancements.

(E6) The Gibbs energy of formation for the hydrogen bond should be greater than the thermal energy of the system for the hydrogen bond to be detected experimentally.

In an embodiment of the present invention, the agent that comprises at least one group capable of forming a hydrogen bond, preferably at least two groups capable of forming a hydrogen bond, comprises at least one of the following groups: hydroxyl groups (OH), carboxyl groups (COOH), amino groups (NH), sulfhydryl groups (SH) and/or hydrogen donor linkages that include, but are not limited to, glycolytic linkages, peptide bonds.

Preferably, these groups are hydroxyl groups, amino groups or sulfhydryl groups.

In accordance with the present invention, the term "fiber" is to be understood as generally referring to threads or threadlike structures and is generally understood to relate to a flexible structure, which is thin in relation to its length. Fibers have a small diameter and can be built up with one another by corresponding bonding processes to produce fibrous structures or fiber materials. In accordance with the present invention, the average diameter of the fibers making up the fiber material is preferably in the range of 50 nm to 1000 µm, preferably 1 µm to 100 µm, further preferably from 5-25 µm.

In accordance with the present invention, the fiber material comprises at least one non-ionic fiber material. A "non-ionic" fiber, in accordance with the present invention, describes a fiber that is substantially not ionizing in aqueous solution at a pH value of 7.

In embodiments of the invention, the amount of agent in the fiber material, relative to the overall weight of the composite material, is from 1% w/w to 40% w/w, preferably from 5% w/w to 35% w/w, further preferably from 15% w/w to 25% w/w.

In embodiments of the invention, the wet tensile strength (as defined below) of the fiber material is increased by at least 5%, preferably at least 10% and further preferably by at least 15%, for a fiber material according to the present invention, compared to an otherwise identical fiber material, which, however, has not been treated with the at least one agent.

In embodiments of the invention, the fiber material comprises an antimicrobial agent, in particular the fiber material comprises:
a substrate of non-ionic, non-woven fibers, preferably a web of non-ionic, non-woven fibers,
at least one additional component, which is an agent that comprises at least one group capable of forming a hydrogen bond, preferably at least two groups capable of forming a hydrogen bond,
at least one antimicrobial agent.

In accordance with the present invention, the antimicrobial agent may be applied, or may be present in the final product, together with the agent having at least one, preferably two groups capable of forming a hydrogen bond. Therefore, the overall fiber material is homogenously improved not only in regard to integrity in the wet state, but also particularly suited for wound treatment.

In embodiments of the invention, the antimicrobial agent comprises silver. In embodiments of the invention, the silver is metallic silver. In embodiments of the invention, the silver is a silver salt. In embodiments of the invention, the silver salt is silver sulfate, silver chloride, silver nitrate, silver sulfadiazine, silver carbonate, silver phosphate, silver lactate, silver bromide, silver acetate, silver citrate, silver CMC, silver oxide. In embodiments of the invention, the silver salt is silver sulfate. In embodiments of the invention, the antimicrobial agent comprises a monoguanide or biguanide. In embodiments of the invention, the monoguanide or biguanide is chlorhexidine digluconate, chlorhexidine diacetate, chlorhexidine dihydrochloride, polyhexamethylene biguanide (PHMB) or a salt thereof, or polyhexamethylene monoguanide (PHMG) or a salt thereof. In embodiments of the invention, the biguanide is PHMB or a salt thereof. In embodiments of the invention, the antimicrobial agent comprises a quaternary ammonium compound. In embodiments of the invention, the quaternary ammonium compound is cetylpyridinium chloride, benzethonium chloride, or polyDADMAC. In embodiments of the invention, the antimicrobial agent comprises triclosan, sodium hypochlorite, copper, hydrogen peroxide, xylitol, or honey.

In embodiments of the invention, the fiber material further comprises an antimicrobial coating that comprises an antimicrobial agent and one or more polymers, wherein the one or more polymers are selected from the group consisting of cellulosic polymers, neutral poly(meth)acrylate esters, polyvinylpyrrolidone, polyvinylpolypyrrolidone, and combinations thereof.

In embodiments of the invention, the fiber material comprises polyvinyl alcohol, preferably wherein the polyvinyl alcohol is cross-linked.

In embodiments of the invention, the one or more polymers in the antimicrobial coating are cellulosic polymers, preferably selected from the group consisting of hydroxypropylmethylcellulose (HPMC), hydroxypropylcellulose (HPC), methylcellulose (MC), and ethylcellulose (EC), preferably hydroxypropylcellulose (HPC). In embodiments of the invention, the one or more polymers in the antimicrobial coating is hydroxypropylcellulose (HPC).

In embodiments of the invention, the antimicrobial agent in the antimicrobial coating is or comprises silver, preferably silver oxide or a silver salt.

In embodiments of the invention, the fiber material further comprises at least one absorbing material, preferably a superabsorbent material, further preferably superabsorbent polymers, further preferably in the form of particles.

The presence of such an (additional) absorbing material allows to further control fluid uptake and management capabilities of the fiber material, which is particularly advantageous in wound treatment.

According to a second aspect of the invention, the above-discussed and other objects are achieved through a process for making a fiber material, comprising the following steps:
  providing at least one non-ionic fiber material, this is present in a non-woven substrate, preferably in a non-woven web;
  bringing said at least one non-ionic fiber material into contact with at least one agent that comprises at least one group capable of forming a hydrogen bond, preferably at least two groups capable of forming a hydrogen bond.

In embodiments of the invention, said process also comprises the following step, which is performed after the "bringing into contact"-step above:
  drying the non-ionic fiber material and the agent as brought into contact with each other.

Preferably, said agent that is brought into contact with at least one non-ionic fiber material, is provided as a compound that is dissolved or distributed in a liquid, in particular in form of a solution, a slurry, an emulsion or the like. In accordance with the present invention, it is particularly preferred if the agent (compound) is present as a solute in a solvent.

However, the direct application of the agent (compound), without a solvent, including in solid form, is also within the scope of the present invention.

In regard to the solvent, no restrictions or limitations exist, except that the solvent must be able to dissolve the agent and the solvent does cause irreversible swelling of the non-ionic fiber material during or after application. Examples of such solvents are, but are not limited to, ethanol, isopropanol and methanol. Ethanol is a preferred solvent.

In accordance with the present invention, the term "bringing into contact" is to be understood to generally relate to methods known to the person skilled in the art as relating to bringing a solid material into physical contact with another material, which may be a solid or a fluid. Examples of such 'bringing into contact' include, but are not limited to: applying a solid or viscous substance by (spray) deposition, calendering, coating, dipping etc. or applying and/or spraying a fluid medium onto a (fiber) material, dipping the (fiber) material into a fluid medium, saturating/soaking of the (fiber) material in a fluid medium, or forming a slurry, suspension or mixture of the (fiber) material with a fluid medium. The fluid medium may for example be a mixture (e.g. suspension or solution) of the agent and at least one of the above discussed solvents.

In accordance with the present invention, it is particularly preferred that the fiber material is impregnated with the at least one agent and/or that the at least one agent is applied onto the fiber material.

In one embodiment of the invention, the fiber material as brought into contact with the at least one agent is exposed to an atmosphere with a partial pressure of the fluid medium lower than the pressure of the pure liquid (i.e. the fluid medium), so that the fluid medium, at least partly, evaporates. Such a lowered pressure can be achieved by means of applying a lowered pressure, including vacuum, for example.

In accordance with the present invention, the 'drying'-step may occur under ambient conditions (i.e. at atmospheric pressure and room temperature), preferably for 6 to 12 hours, or may occur at elevated temperature and/or under reduced pressure.

The fiber materials according to the invention exhibit improved properties vis-à-vis known fiber materials. While the fiber materials in accordance with the present invention may not show all of the potential improvements discussed in the following, or not all to the same extent or to the fullest extent, the following improvements are generally found in materials in accordance with the present invention.

As already alluded to above, the integrity of fiber materials in the wet state is of particular importance. One way to measure this 'integrity' or 'stability' is to measure the wet tensile strength (as defined in more detail below) of such a fiber material.

The inventors have found that the fiber materials according to the present invention, comprising at least one additional component (additional to the non-ionic fiber material), which is an agent that comprises at least one group capable of forming a hydrogen bond, preferably at least two groups capable of forming a hydrogen bond, wherein the non-ionic fiber material and the agent are linked by means of hydrogen bonds, have increased wet tensile strength vis-à-vis an otherwise identical fiber material, which, however, does not comprise said agent, and/or has not been brought into contact with said agent.

Figure 1:
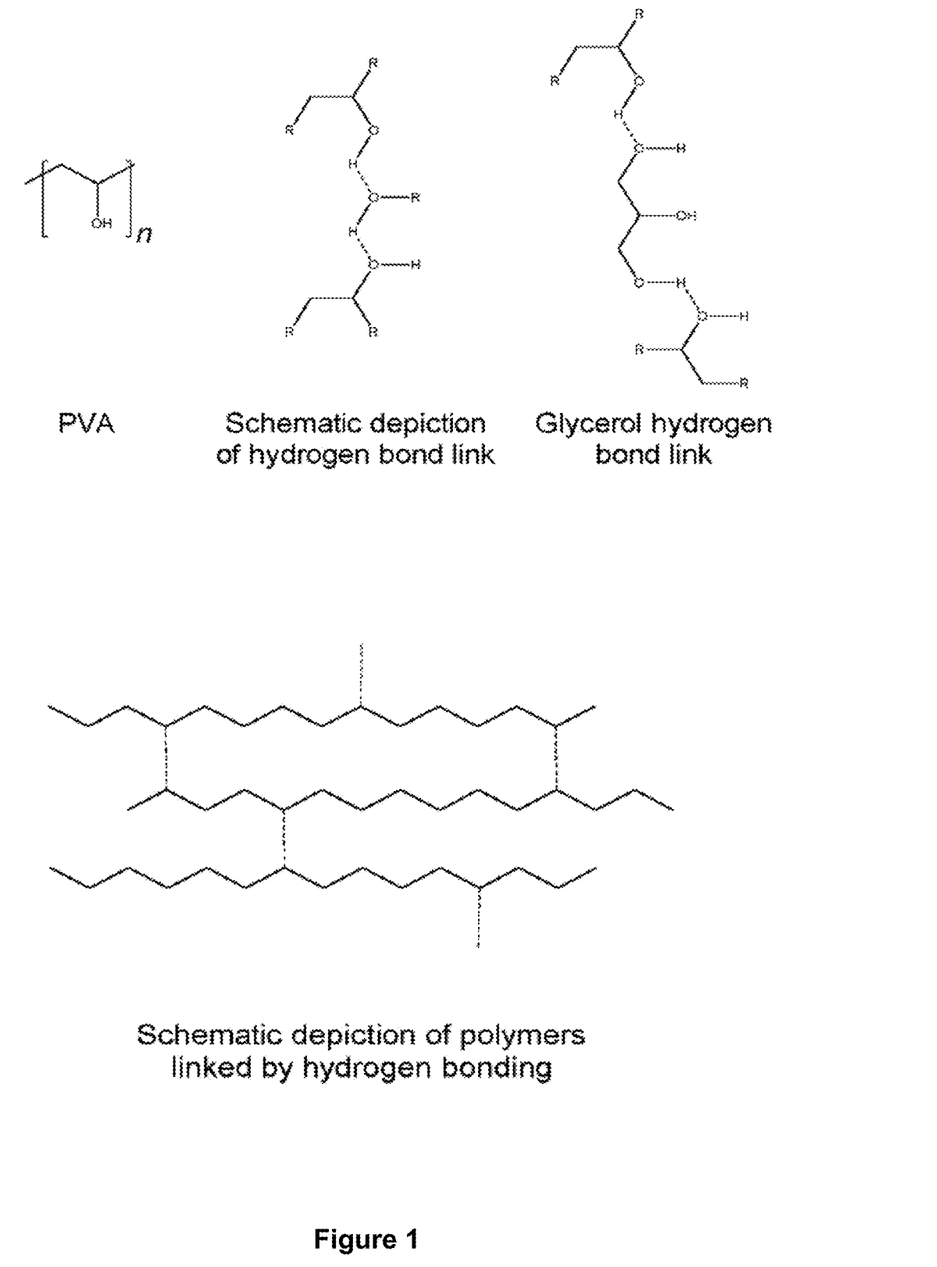
FIG. 1 is a schematic depiction of PVA, a hydrogen bond link, a glycerol hydrogen bond link, and polymers linked by hydrogen bonding.

Without wishing to be bound by theory, the inventors believe that the improved (mechanical) properties of a non-ionic fiber material, in which the non-ionic fiber material has been brought into contact with (treated with) the at least one agent comprising at least one, preferably two, group(s) capable of forming a hydrogen bond is due to the formation of hydrogen bonds between the backbone of the polymer making up the fiber material and the hydrophilic groups of the agent. This mechanism is believed to contribute to improved properties, such as improved wet strength, gelling speed and keeping the product from drying out too quickly. This effect is schematically illustrated for stabilizing a PVA backbone by way of forming hydrogen bonds with glycerol (see FIG. 1).

The term "wet tensile strength" is to be understood as the maximum tensile force per unit width, as measured in accordance with EN 29073-3:1992 (with amendments as specified below), that a test piece will stand, in a wet state having absorbed a maximum amount of Solution A according to the "Free swell absorptive capacity method" EN 13726-1 (with an absorption time of 10±1 minutes at 23±2° C.), before it breaks apart in said tensile strength test.

Figure 2:
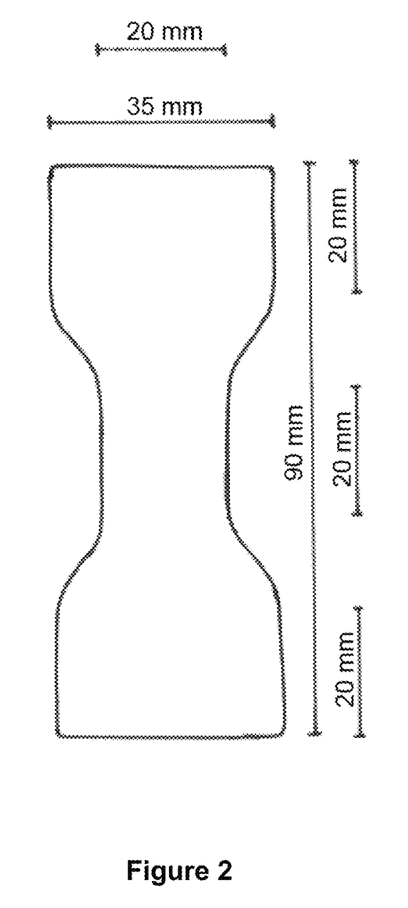
FIG. 2 is a schematic depiction of a test piece sample used for measuring "wet tensile strength" according to modified EN 29073-3:1992.

The method of measuring the "wet tensile strength", according to the invention, is modified vis-à-vis EN 29073-3:1992 in the following manner: i) the material is soaked according to EN 13726-1 (with an absorption time of 10±1 minutes at 23±2° C. and before cutting the test piece); ii) the test piece is cut according to FIG. 2 giving a width of 20 mm; iii) a gauge length of 50 mm (i.e. distance between jaws according to section 7.2 of EN 29073-3:1992) is used; and iv) method is performed at a temperature of 23±2° C. and 50±5% rh. These deviations are all allowable alterations of EN 29073-3:1992 (see, e.g., notes in sections 6 and 7 of EN 29073-3:1992).

Solution A, as defined in EN 13726-1, consists of a sodium chloride and calcium chloride solution containing 142 mmol of sodium ions and 2.5 mmol of calcium ions as the chloride salts. This solution has an ionic composition comparable to human serum or wound exudate. Said solution is prepared by dissolving 8,298 g of sodium chloride and 0.368 g of calcium chloride dihydrate in deionized water up to the "1 L" marking in a volumetric flask.

According to another aspect, products comprising gel-forming fiber materials, i.e. fiber materials that expand when exposed to fluids, may get stiff(er) when they dry out, for example due to a decreased flow of wound exudate. This may cause discomfort and/or pain to the patient, especially during dressing changes. The inventors have found that the fiber materials according to the present invention, comprising at least one additional component (additional to the non-ionic fiber material), which is an agent that comprises at least one group capable of forming a hydrogen bond, preferably at least two groups capable of forming a hydrogen bond, wherein the non-ionic fiber material and the agent are linked by means of hydrogen bonds, are less likely to get stiff and are therefore perceived to be "softer" and more comfortable for the patient compared to the otherwise identical fiber material that does not comprise said agent and/or has not been brought into contact with said agent.

In embodiments of the invention and in order to efficiently absorb exudate, the non-ionic fiber material should be at least partly hydrophilic. In case the starting materials are not (sufficiently) hydrophilic, in particular if the fiber material appears to not absorb water rapidly enough, also in regard to its macroscopic behavior, in some embodiments the fiber material is treated to be (more) hydrophilic, for example by means of plasma treatment. Under certain circumstances, this treatment may lose its effectiveness over time. The inventors have found that the fiber materials according to the present invention, comprising at least one additional component (additional to the non-ionic fiber material), which is an agent that comprises at least one group capable of forming a hydrogen bond, preferably at least two groups capable of forming a hydrogen bond, are less likely to lose hydrophilic properties over time-of-use, compared to the otherwise identical fiber material that does not comprise said agent, and/or has not been brought into contact with said agent.

In accordance with the present invention, the term "hydrophilic" is to be understood as defined in IUPAC: Compendium of Chemical Terminology, 2nd ed. (the "Gold Book"), compiled by A. D. McNaught and A. Wilkinson. Blackwell Scientific Publications, Oxford (1997), ISBN 0-9678550-9-8, as generally referring to the capacity of a molecular entity or of a substituent to interact with polar solvents, in particular with water, or with other polar groups.

Wound dressings comprising hydrophilic fiber materials known from the art may not form a gel instantly, or not as fast as desired. This is generally perceived as a disadvantage. The inventors have found that the fiber materials according to the present invention have improved gel-forming properties compared to an otherwise identical fiber material that does not comprise an agent that comprises at least one, preferably two groups capable of forming a hydrogen bond, and/or has not been brought into contact with said agent.

While the present invention is primarily exemplified and illustrated in the context of wound treatment/wound care, the fiber materials of the present invention are generally suitable for all uses, in which fiber materials of increased strength and integrity are advantageous, included but not limited to use as substrate/carrier materials, use in household products and use in cosmetics or hygiene articles, for examples female hygiene articles, diapers, absorbent pads etc.

Therefore, in a third aspect, the present invention relates to a fiber material in accordance with the present invention, or produced in accordance with the present invention, as or in substrate/carrier materials, for use in household products, for use in cosmetics or hygiene articles, in particular female hygiene articles, diapers, absorbent pads, or for use in wound treatment.

The use in wound care/wound treatment, includes the care/treatment of open or closed wounds, for example, including, inter alia (but not limited to), chronic wounds, acute wounds, and post-operative wounds such as e.g. closed incisions or scar treatment.

The fiber materials of the present invention are capable to absorb and retain a liquid and may be used 'stand-alone' [i.e. without the presence of another (super)absorbent] material, in any uses requiring absorption capabilities. However, in embodiments of the present invention, the fiber materials are used together with an additional absorbing material, in particular superabsorbent materials, in particular superabsorbent polymers, preferably in the form of particles.

DESCRIPTION OF EMBODIMENTS OF THE INVENTION

Without limitation, suitable non-ionic fiber materials include or are polyvinyl alcohol, polysaccharides, and polymers comprising polyethylene glycol (PEG) and/or polypropylene glycol, for example polyurethane with PEG functionalities, such as the polymer fibers disclosed in WO 2013/041620.

In some embodiments, the non-ionic fiber material is or comprises a polyvinyl alcohol. In some embodiments the non-ionic fiber materials comprises a plurality of fibers comprising polyvinyl alcohol, such as the plurality of fibers disclosed in US 2013/0323195 and/or US 2013/0274415, the content of which relating to fiber materials is hereby incorporated by reference.

In some embodiments, the non-ionic fiber material comprises a polyurethane polymer with polyethylene glycol (PEG) and/or polypropylene glycol functionalities, such as the polymer fibers disclosed in WO 2013/041620.

In preferred embodiments of the present invention, said non-ionic fiber material is or comprises polyvinyl alcohol. At least one polyvinyl alcohol copolymer may also be used. In the case of a polyvinyl alcohol copolymer, polyethylene vinyl alcohol may be used, for example.

If polyvinyl alcohol copolymers are used as non-ionic fiber materials, the properties of the fibers may be adjusted in a targeted manner as appropriate. Thus in the event of use of, for example polyethylene vinyl alcohol, the number of OH groups may be reduced. However, other functional groups may also be introduced into the fibers by means of copolymerisation. Thus, polyvinyl alcohol copolymers make further non-ionic fiber materials available.

Polyethylene vinyl alcohol, polyvinyl alcohol styrene, polyvinyl alcohol vinyl acetate, polyvinyl alcohol vinyl pyrrolidone, polyvinyl alcohol ethylene glycol and/or polyvinyl alcohol, particularly preferably polyethylene vinyl alcohol, polyvinyl alcohol vinyl acetate, polyvinyl alcohol vinyl pyrrolidone, polyvinyl alcohol vinylamine, polyvinyl alcohol acrylate, polyvinyl alcohol acrylamide, polyvinyl alcohol ethylene glycol and/or polyvinyl alcohol and particularly preferably polyvinyl alcohol may all be used as a non-ionic fiber material, in accordance with the present invention. Block copolymers and/or graft copolymers and/or block and graft copolymers, statistical or alternating systems and any mixtures of these are used as non-ionic fiber material.

A polyvinyl alcohol copolymer may be used in unsubstituted or in partially substituted form. In the event of partial substitution, partial substitution of the OH groups by —O(C═O)—R or —OR is included, wherein R, in each case independently of one another, stands for a C1-C4 alkyl group. In this case a C1-C4 alkyl group is understood to be methyl, ethyl, propyl, iso-propyl, 1-butyl, 2-butyl, or tert-butyl.

Furthermore the non-ionic fiber material may be formed as a polymer blend. In this case a polymer blend is understood to be a physical mixture of at least two polymers from the melt or from the solution.

In order to form such a polymer blend, further polymers may be used, such as for example alginates, cellulose ethers, such as carboxymethyl celluloses, methyl celluloses, ethyl celluloses, hydroxymethyl I celluloses, hydroxyethyl celluloses, hydroxyalkyl methylcelluloses, hydroxypropyl celluloses, cellulose esters, such as cellulose acetate, oxidised celluloses, bacterial celluloses, cellulose carbonates, gelatines, collagens, starches, hyaluronic acids, pectins, agar, polyacrylates, polyvinyl amines, polyvinyl acetates, polyethylene glycols, polyethylene oxides, polyvinyl pyrrolidones, polyurethanes or nongelling further polymers, such as for example polyolefins, celluloses, cellulose derivatives, regenerated celluloses such viscoses, polyamides, polyacrylonitriles, polyvinyl chlorides, chitosans, polylactides, polyglycolides, polyester amides, polycaprolactones, polyhexamethylene terephthalates, polyhydroxybutyrates, polyhydroxyvalerates or polyesters.

In some embodiments, the non-ionic fiber material comprises a polymer that is cross-linked, in particular cross-linked polyvinyl alcohol. The term "cross-linked" is used herein to describe a material comprising a plurality polymer molecules which are interlinked by a chemical bond, in particular a covalent bond or an ionic bond, or by a physical cross-link, such as in thermoplastic elastomers.

In some embodiments, the non-ionic fiber material is cross-linked by heat or chemical treatment, in particular by heat. Cross-linked non-ionic fiber materials are capable of forming a swollen coherent gel upon absorbing a liquid. Thereby, a wound dressing substrate comprising such a fiber material can be removed coherently from a wound. Using non-ionic fiber material that is (already) crosslinked is in accordance with the present invention, in regard to which it is believed (see discussion below) that the bringing into contact of the non-ionic fiber material with the at least one agent comprising one, preferably two, group(s) capable of forming a hydrogen bond, results in (further) crosslinking of the non-ionic fiber material.

Overall, in embodiments of the present invention, the non-ionic fiber material comprises or consists of polyvinyl alcohol (PVA), preferably cross-linked PVA, polysaccharides, and/or polyurethane polymer with polyethylene glycol (PEG) and/or polypropylene glycol functionalities, and/or copolymers thereof.

In some embodiments, a fiber material according to the present invention, in particular a wound dressing substrate comprising the fiber material according to the present invention, in a wet state having absorbed a maximum amount of Solution A according to EN 13726-1 (with an absorption time of 10±1 minutes and at a temperature of 23±2° C.), has a wet tensile strength of at least 0.2 N/2 cm as measured by EN 29073-3:1992 (with the modifications as specified above).

In some embodiments, the fiber material according to the present invention, in particular a wound dressing substrate in a wet state as defined above, has a wet tensile strength (as defined above) of at least 0.2 N/2 cm preferably at least 0.6 N/2 cm or at least 0.8 N/2 cm or at least 1.0 N/2 cm, or at least 1.5 N/2 cm, or at least 2 N/2 cm, further preferably at least 2.5 N/2 cm, or at least 3 N/2 cm, for example at least 4 N/2 cm such as at least 5 N/2 cm or at least 6 N/2 cm or at least 7 N/2 cm or at least 8 N/2 cm or at least 9 N/2 cm, or at least 10 N/2 cm, further preferably at least 15 N/2 cm such as at least 20 N/2 cm or at least 25 N/2 cm. Fulfilling such "minimal" requirements for the wet tensile strength is of particular importance in wound treatment, where disintegration of a wound dressing when wet is a situation that should be avoided.

In some embodiments, the fiber material according to the present invention, in particular a wound dressing substrate in a wet state as defined above, has a wet tensile strength (as defined above) of from 0.2 to 15 N/2 cm. In some embodiments, the fiber material according to the present invention, in particular the wound dressing substrate in a wet state, has a wet tensile strength (as defined above) of from 1 to 10 N/2 cm. In some embodiments, the fiber material according to the present invention, in particular the wound dressing substrate in a wet state as defined above, has a wet tensile strength (as defined above) of from 2 to 10 N/2 cm.

As used herein, the term "wound dressing substrate in a wet state", should be understood as a wound dressing substrate which has been wetted (or soaked) to maximum absorptive capacity according to EN 13726-1:2002 (with absorption time of 10±1 minutes and at a temperature of 23±2° C.). Thus, the tensile strength as given herein refers to the tensile strength as measured on such wet wound dressing substrate and/or on a fiber material according to the present invention.

In some embodiments, the wet tensile strength (as defined above) is increased by at least 5%, preferably at least 10% and further preferably by at least 15%, for a fiber material according to the present invention, compared to an otherwise identical fiber material, which, however, has not been treated with the at least one agent comprising at least one group capable of forming a hydrogen bond, preferably at least two groups capable of forming a hydrogen bond.

In principle, no limitation exist in regard to the agent that comprises at least one group capable of forming a hydrogen bond, preferably at least two groups capable of forming a hydrogen bond. Said agent is preferably a compound, which compound can either be a monomer/small molecule or a polymer.

In some embodiments, the agent that comprises at least one group capable of forming a hydrogen bond, preferably at least two groups capable of forming a hydrogen bond, is selected from the group consisting of polyols, in particular sugar alcohols (sugar polyols), polymeric polyols; polysaccharides, alpha-hydroxy acids; cellulose ethers or cellulose esters; di- or polyisocyanates; polyethers or polyesters.

Non-limiting examples of such agents are: glycol, propylene glycol, glycerol, sorbitol, xylitol, maltitol, hexylene glycol, butylene glycol, glyceryl triacetate, polydextrose, lactic acid, panthtothenic acid, hyaluronic acid, sodium-2-pyrrolidone-5-carboxylate ('sodium PCA'), polyethylene glycol (PEG) (also known as polyethylene oxide or polyoxyethylene), polypropylene glycol (PPG), polyvinylpyrrolidone (PVP), (also known as polyvidone or povidone).

In some embodiments, the agent that comprises at least one group capable of forming a hydrogen bond, preferably at least two groups capable of forming a hydrogen bond, is glycerol or polyethylene glycol.

As already discussed above, the non-ionic fibers in accordance with the present invention preferably increase in fiber diameter upon contact with a fluid/moisture, i.e. gel during use and/or at the point of use. A gel should be understood to be a finely dispersed system consisting of at least one solid and one liquid phase, wherein the solid phase forms a three-dimensional network the pores of which are filled by the liquid phase. Both phases penetrate one another essentially completely and consequently may store a liquid phase, for example an exudate, in a more stable manner with respect to, for example, pressure. Fibers or fibrous structures according to the present invention are preferably chosen to be gelling, in particular hydrogelling, and consequently have an outstanding retention capacity for corresponding liquid phases. Fibers or fibrous structures according to the present invention are preferably applied in a dry state to the wound and they form stable gels with the wound exudate, thus creating a moist wound climate. Such a moist wound treatment may assist the healing process.

Likewise, for moist wound treatment fibers or fibrous structures according to the present invention can be used in gel form with a liquid phase. In this case water is preferably used as liquid phase and particularly preferably a 0.9% aqueous sodium chloride solution, Ringer solution or solutions containing an active substance. Consequently gelling should be understood as the ability to form a gel by absorbing a liquid phase, and hydrogelling should be understood as the ability to form a hydrogel, which has as liquid phase water or an aqueous solution, particularly preferably a 0.9%, aqueous sodium chloride solution.

In some embodiments of the invention, the fiber material in accordance with the present invention has a free swell absorptive capacity, corresponding to the maximum absorptive capacity of the fiber material in accordance with the present invention, of at least 1 times its own weight as measured by EN 13726-1:2002 ("Free swell absorptive capacity"). For example, in some embodiments, the fiber material in accordance with the present invention has a free swell absorptive capacity, corresponding to the maximum absorptive capacity of the fiber material in accordance with the present invention, of at least 3 times its own weight as measured by EN 13726-1:2002. For example, in some embodiments, the fiber material in accordance with the present invention has a free swell absorptive capacity, corresponding to the maximum absorptive capacity of the fiber material in accordance with the present invention, of at least 5 times its own weight as measured by EN 13726-1:2002. For example, in some embodiments, the fiber material in accordance with the present invention has a free swell absorptive capacity, corresponding to the maximum absorptive capacity of the fiber material in accordance with the present invention, of at least 10 times its own weight as measured by EN 13726-1:2002. For example, in some embodiments, the fiber material in accordance with the present invention has a free swell absorptive capacity, corresponding to the maximum absorptive capacity of the fiber material in accordance with the present invention, of at least 15 times its own weight as measured by EN 13726-1:2002. For example, in some embodiments, the fiber material in accordance with the present invention has a free swell absorptive capacity, corresponding to the maximum absorptive capacity of the fiber material in accordance with the present invention, of at least 20 times its own weight as measured by EN 13726-1:2002. For example, in some embodiments, the fiber material in accordance with the present invention has a free swell absorptive capacity, corresponding to the maximum absorptive capacity of the fiber material in accordance with the present invention, of at least 25 times its own weight as measured by EN 13726-1:2002.

In some embodiments, the substrate comprises absorbent particles. In some embodiments, the absorbent particles are dispersed within the fiber material. In some embodiments, the substrate also includes non-absorbent fibers. In some embodiments, the absorbent fibers and/or absorbent particles are airlaid by spraying, needling, or carding together with non-absorbent fibers.

The advantages of the invention have been demonstrated in the following Examples.

EXAMPLES

Example 1—Preparation of Samples

Formulations, as outlined in Table 1, were prepared by adding a respective amount of each agent, including glycerol (commercially available from Sigma-Aldrich), PEG 200 (commercially available from Alfa Aesar), and PEG 400 (commercially available from Alfa Aesar), to ethanol (200 proof, commercially available from Merck). The formulations were stirred for 15 minutes at room temperature.

Exufiber® (commercially available from Mölnlycke Health Care; size: 20×30 cm, 250 gsm), which is a non-ionic and nonwoven fiber dressing comprising (non-ionic) cross-linked polyvinyl alcohol fibers, was treated with the different formulations by adding the formulation (0.15 g/cm$^2$) using a pipette to thereby produce samples with the different agents at increasing concentrations of agents as disclosed in Table 1. Subsequently, the samples were dried at room temperature for 3 days (before further testing according to Example 2, see below).

In addition, Aquacel® (commercially available from ConvaTec, size: 15×15 cm, 100 gsm), which a nonwoven but ionic (charged) fiber dressing comprising carboxymethyl cellulose (CMC) fibers in ionic form (e.g. as the sodium salt), was treated (0.15 g/cm$^2$) using a pipette with the glycerol formulations, and subsequently dried at room temperature for 3 days, to produce Aquacel® test samples comprising glycerol at different concentrations, as disclosed in Table 1. References samples with both Exufiber® and Aquacel® was also prepared, without adding the agent according to the present invention but instead treated accordingly with 100% ethanol and subsequently dried.

Example 2

The wet tensile strength was tested according to the following method: samples (size should be large enough to fit the punching tool after possible shrinkage on absorption) were prepared as described above (see example 1) and were first allowed to absorb (for 10±1 min) a maximum amount of Solution A according to EN 13726-1:2002. The samples were placed on a cutting board and punched out, in nonwoven machine direction, with a necking punch according to FIG. 2. The wet tensile strength of the samples was measured using a tensile testing instrument (Zwick Z005 TE) with a cross head speed of 100 mm/min and a gauge length of 50 mm.

The result of the wet tensile strength testing according to Example 2 is shown in Table 1 below. Each testing was performed in triplicate, respectively, and the value presented in Table 1 is thus the calculated average value.

TABLE 1

| Test Sample | Formulations (% w/w agent in EtOH) | Agent conc. in dried test sample (% w/w) | Wet tensile strength (N/20 mm) |
|---|---|---|---|
| 1 | 0% agent (100% EtOH) | Exufiber ® (no agent added) | 2.27N/20 mm |
| 2 | Glycerol; 1.45% | Exufiber ® 8% glycerol | 2.37N/20 mm |
| 3 | Glycerol; 4.16% | Exufiber ® 20% glycerol | 2.94N/20 mm |
| 4 | Glycerol; 8.97% | Exufiber ® 35% glycerol | 3.71N/20 mm |
| 5 | PEG200; 8.97% | Exufiber ® 35% PEG200 | 3.10N/20 mm |
| 6 | PEG400; 8.97% | Exufiber ® 35% PEG400 | 3.29N/20 mm |
| 7 | 0% agent (100% EtOH) | Aquacel ® (no agent added) | 0.38N/20 mm |
| 8 | Glycerol; 1.67% | Aquacel ® 20% glycerol | 0.32N/20 mm |
| 9 | Glycerol; 3.59% | Aquacel ® 35% glycerol | 0.38N/20 mm |

As can be seen, for the Exufiber® nonwoven fiber dressing, adding glycerol surprisingly improved the wet tensile strength of the fibers significantly with an increase of 4.4% for 8% w/w glycerol, 29.5% for 20% w/w glycerol, and 63.4% for 35% w/w glycerol, as compared with the tensile strength of the reference Exufiber® sample (no agent). Also, the test samples with 35% w/w PEG200 and 35% w/w PEG400 showed a significant and equally surprisingly improved wet tensile strength with an increase of 36.5% and 44.9%, respectively. In contrast, the Aquacel® samples treated with glycerol (20% w/w and 35% w/w, respectively) did not result in an increased wet tensile strength.

Without wishing to be bound by theory, it is believed that the non-ionic nature of the crosslinked polyvinyl alcohol fibers facilitates chemical interaction with the agent, for example, by hydrogen bonding interaction between the hydroxyl groups on the polyvinyl alcohol fiber and the hydroxyl groups of the agents, thus creating hydrogen bonding bridges (e.g. cross-linkages) between polyvinyl alcohol polymer chains in the fibers.

Example 3

Gelling time was measured using a stop watch by visual inspection of the samples 1 to 4 (prepared as described above) after soaking in Solution A according to EN 13726-1:2002.

The stop watch was started at the same time as the sample was soaked. When the samples turned into a transparent gel from their original fibrous state the time was recorded.

As can be seen in Table 2, impregnation of Exufiber® with the agent in accordance with the present invention significantly reduces the gel time in contact with aqueous solution. Thereby, faster absorption is achieved.

TABLE 2

| Sample | Gelling time |
|---|---|
| 1: Exufiber ® (no agent added) | 27 sec |
| 2: Exufiber ® 8% glycerol | 15 sec |
| 3: Exufiber ® 20% glycerol | 12 sec |
| 4: Exufiber ® 35% glycerol | 11 sec |

All Examples 1 to 3 were performed at a temperature of 23±2° C. and 50±5% relative humidity.

The invention claimed is:

1. A fiber material comprising:
   a substrate of non-ionic, non-woven fibers, and
   at least one additional component, which is an agent that comprises at least one group capable of forming a hydrogen bond,
   wherein a combination of the substrate and the agent causes the fiber material to have an increased wet tensile strength of at least 5%, as measured in accordance with EN 29073-3:1992, as compared to an otherwise identical fiber material without the agent.

2. The fiber material according to claim 1, wherein the combination of the substrate and the agent causes the fiber material to have an increased wet tensile strength of at least 10%, as measured in accordance with EN 29073-3:1992, as compared to an otherwise identical fiber material without the agent.

3. The fiber material according to claim 2, wherein the non-ionic, non-woven fibers are crosslinked by the agent.

4. The fiber material according to claim 1, wherein the combination of the substrate and the agent causes the fiber material to have an increased wet tensile strength of at least 15%, as measured in accordance with EN 29073-3:1992, as compared to an otherwise identical fiber material without the agent.

5. The fiber material according to claim 4, wherein the non-ionic, non-woven fibers are crosslinked by the agent.

6. The fiber material according to claim 1, wherein the fiber material has a wet tensile strength of at least 2.5 N/2 cm, as measured in accordance with EN 29073-3:1992.

7. The fiber material according to claim 1, wherein the fiber material has a wet tensile strength of at least 3.0 N/2 cm, as measured in accordance with EN 29073-3:1992.

8. The fiber material according to claim 1, wherein the fiber material has a wet tensile strength of at least 4.0 N/2 cm, as measured in accordance with EN 29073-3:1992.

9. The fiber material according to claim 1, wherein the non-ionic, non-woven fibers comprises polyvinyl alcohol (PVA), a polysaccharide, and/or a polyurethane polymer with polyethylene glycol (PEG) and/or polypropylene glycol functionalities, and/or copolymers thereof.

10. The fiber material according to claim 1, wherein the agent that comprises the at least one group capable of forming a hydrogen bond comprises at least one of the following groups: a hydroxyl group, a carboxyl group, an amino group, a sulfhydryl group, and/or hydrogen donor linkages comprising a glycolytic linkage, or a peptide bond.

11. The fiber material according to claim 1, wherein an amount of agent in the fiber material, relative to the overall weight of the fiber material, is from 1% w/w to 40% w/w.

12. The fiber material according to claim 1, further comprising at least one antimicrobial agent.

13. The fiber material according to claim 1, further comprising at least one absorbing material.

14. The fiber material according to claim 1, wherein the substrate of non-ionic, non-woven fibers is a web of non-ionic, non-woven fibers.

15. The fiber material according to claim 1, wherein the substrate of non-ionic, non-woven fibers comprises cross-linked PVA.

16. The fiber material according to claim 1, further comprising at least one superabsorbent material in the form of particles.

17. The fiber material according to claim 1, wherein the amount of agent in the fiber material, relative to the overall weight of the fiber material, is from 15% w/w to 25% w/w.

18. The fiber material according to claim 1, wherein the agent comprises at least two groups capable of forming a hydrogen bond.

* * * * *